US012411137B2

United States Patent
Liu et al.

(10) Patent No.: US 12,411,137 B2
(45) Date of Patent: Sep. 9, 2025

(54) VIRUS COLLECTION MATRIX

(71) Applicant: National Yang Ming Chiao Tung University, Hsinchu (TW)

(72) Inventors: Dean-Mo Liu, Zhubei (TW); Yung-Hsin Chang, Hsinchu (TW); Wen-Lien Wang, Hsinchu (TW); Shu-Han Liu, Hsinchu (TW)

(73) Assignee: NATIONAL YANG MING CHIAO TUNG UNIVERSITY, Hsinchu (TW)

( * ) Notice: Subject to any disclaimer, the term of this patent is extended or adjusted under 35 U.S.C. 154(b) by 1135 days.

(21) Appl. No.: 17/336,883

(22) Filed: Jun. 2, 2021

(65) Prior Publication Data

US 2022/0205988 A1 Jun. 30, 2022

(30) Foreign Application Priority Data

Dec. 25, 2020 (TW) ............................... 109146136

(51) Int. Cl.
| | | |
|---|---|---|
| *G01N 33/566* | (2006.01) | |
| *C07K 14/705* | (2006.01) | |
| *C07K 17/04* | (2006.01) | |
| *C07K 17/10* | (2006.01) | |
| *C12N 9/48* | (2006.01) | |
| *G01N 15/06* | (2024.01) | |
| *G01N 15/075* | (2024.01) | |
| *G01N 33/548* | (2006.01) | |
| *G01N 33/569* | (2006.01) | |
| *H04W 88/02* | (2009.01) | |

(52) U.S. Cl.
CPC ......... *G01N 33/566* (2013.01); *C07K 14/705* (2013.01); *C07K 17/04* (2013.01); *C07K 17/10* (2013.01); *C12N 9/485* (2013.01); *C12Y 304/17023* (2013.01); *G01N 15/0618* (2013.01); *G01N 33/548* (2013.01); *G01N 33/56983* (2013.01); *G01N 15/075* (2024.01); *G01N 2333/165* (2013.01); *H04W 88/02* (2013.01)

(58) Field of Classification Search
CPC ............ G01N 15/0618; G01N 15/075; G01N 33/548; G01N 33/566; G01N 33/56983; G01N 2333/165; C07K 14/705; C07K 17/04; C07K 17/10; C12N 9/485; C12Y 304/17023; H04W 88/02
See application file for complete search history.

(56) References Cited

U.S. PATENT DOCUMENTS

| | | | |
|---|---|---|---|
| 8,057,993 B2 | 11/2011 | Ecker et al. | |
| 2006/0121580 A1* | 6/2006 | Ter Meulen | A61P 37/02 435/6.16 |
| 2007/0248949 A1 | 10/2007 | Inoue et al. | |
| 2008/0194422 A1 | 8/2008 | Lim et al. | |
| 2021/0387143 A1* | 12/2021 | Doyle | G01N 33/56983 |
| 2022/0018839 A1* | 1/2022 | Al Ahmad | G01N 21/47 |

FOREIGN PATENT DOCUMENTS

| | | | | |
|---|---|---|---|---|
| CA | 3173418 A1 | * | 10/2021 | ......... G01N 21/6428 |
| CN | 1826356 A | | 8/2006 | |
| CN | 103484565 B | | 6/2016 | |
| EP | 1 642 978 A1 | | 4/2006 | |

OTHER PUBLICATIONS

Guliy et al., "Progress in the use of an electro-optical sensor for virus detection", Optics Communications, vol. 465, Jun. 15, 2020, 125605, total of 2 pages.
Jacobi et al., "Low-Frequency Raman Spectroscopy as a Diagnostic Tool for COVID-19 and other Coronaviruses", Royal Society Open Science, Apr. 7, 2020, pp. 1-11.
Jiang et al., "Quantitative Analysis of Severe Acute Respiratory Syndrome (SARS)-associated Coronavirus-infected Cells Using Proteomic Approaches", Molecular & Cellular Proteomics 4.7, The American Society for Biochemistry and Molecular Biology, Inc., 2005, pp. 902-913.
Khan et al., "Spectroscopy as a tool for detection and monitoring of Coronavirus (COVID-19)", Expert Review of Molecular Diagnostics, 2020, pp. 1-3.
Luis Felipe das Chagas e Silva de Carvalho and Marcelo Saito Nogueira, "Optical techniques for fast screening—Towards prevention of the coronavirus COVID-19 outbreak", Photodiagnosis and Photodynamic Therapy, Jun. 30, 2020, 101765, pp. 1-2.

* cited by examiner

*Primary Examiner* — John Kim
(74) *Attorney, Agent, or Firm* — Birch, Stewart, Kolasch & Birch, LLP

(57) ABSTRACT

The present invention provides a virus collection matrix, including: a porous gel or fibrous structure formed by a positively charged polymer material; and a plurality of ACE 2 receptors. The plurality of ACE 2 receptors are negatively charged, and distributed and covered on the surface of the porous gel or fibrous structure. The whole virus collection matrix is positively charged.

13 Claims, 7 Drawing Sheets

VIRUS COLLECTION MATRIX

BACKGROUND OF THE INVENTION

1. Field of the Invention

Figure 1:
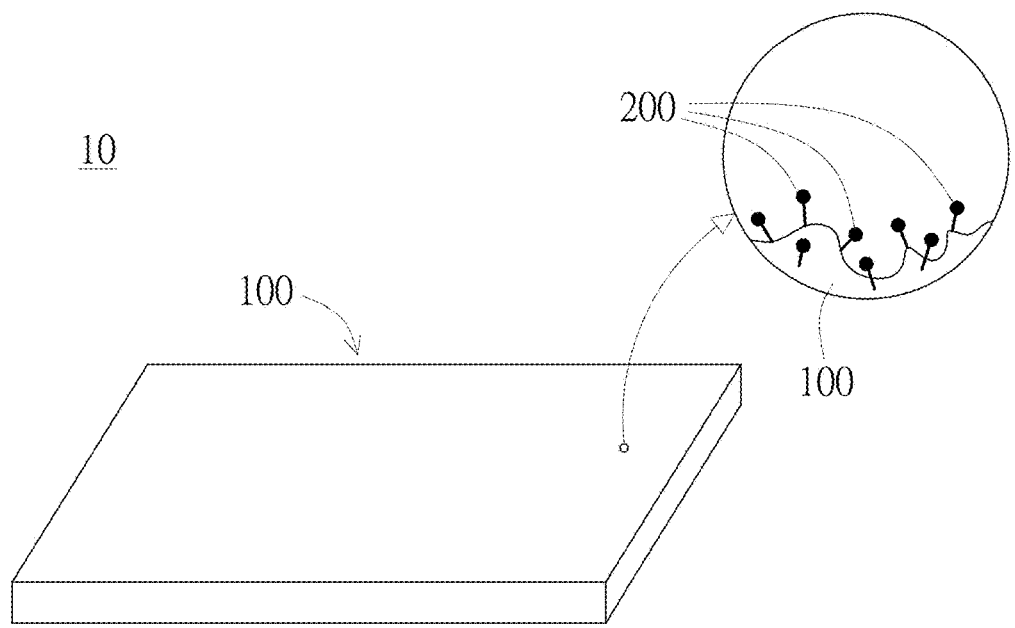

The present disclosure relates to a virus collection matrix. Specifically, the present disclosure relates to a virus collection matrix having ACE 2 receptors.

2. Description of the Prior Art

Novel coronavirus (covid-19) pandemic has caused serious losses of human lives and economic losses around the world; and numbers of confirmed cases and deaths are still increasing and not expected to be eased. For this significant human crisis, scientists around the world are actively dedicated to the research to develop medicines and vaccines against the novel coronavirus (covid-19) so as to save lives of people and contain the spread of the virus. However, research and development of medicines and vaccines still encounter many difficulties and obstacles to be overcome and there is still a lot of uncertainty under a goal of fighting against the novel coronavirus effectively and not causing adverse side effects to human bodies.

As mentioned above, under a situation that research, development and popularization of medicines and vaccines are still uncertain, determination, controlling, and early warning of risks of virus infection also become one of the most important issues at present, and there is huge demand and urgency all over the world regarding to this. Therefore, in addition to technologies related to detection of individual infections, therapies, or establishing immunity, it is also essential to establish a device or a method which can determine, control, and conduct early warning of the risks of virus infection in order to prevent virus infection and maintain normal social operations.

SUMMARY OF THE INVENTION

Technical Means for Solving the Problems

In order to solve the aforementioned problem, an embodiment according to the present disclosure provides a virus collection matrix, comprising: a porous gel or fibrous structure formed by a positively charged polymer material; and a plurality of ACE 2 receptors. The plurality of ACE 2 receptors are negatively charged, and distributed and covered on a surface of the porous gel or fibrous structure. A whole of the virus collection matrix is positively charged.

Another embodiment of the present disclosure provides a manufacturing method of virus collection matrix, comprising following steps: dissolving chitosan into an aqueous solution and adding acetic acid to dissolve chitosan completely so as to form a first solution; adding glycerol and beta-glycophosphate into the first solution so as to form a second solution; letting the second solution stand for a predetermined time until the second solution forms a solid gel (gelation); lyophilizing the solid gel so as to form a porous gel or fibrous structure; and distributing and covering a plurality of ACE 2 receptors on a surface of the porous gel or fibrous structure, and connecting the plurality of ACE 2 receptors to the porous gel or fibrous structure by electric charge attraction or chemical grafting. Alternatively, the second solution can be evolved into ultrafine fibrous mats using an electrospinning equipment, either free standing mats or deposited onto a given substrate.

Another embodiment of the present disclosure provides a detection method for detecting target virus, comprising: disposing the above virus collection matrix under a test environment within a predetermined duration; withdrawing the virus collection matrix and conducting optical analysis to the virus collection matrix directly or conducting optical analysis to an analyte absorbed on the virus collection matrix after taking off the analyte; determining whether the spectral characteristic peak of spike protein is detected or not so as to determine whether the target virus including a spike protein exists in the test environment or not.

Technical Effect as Compared with the Prior Art

The detection of the virus nowadays is basically conducted to those who might be infected through quantitative detection methods such as nucleic acid amplification testing, and antibody detection. These methods consume a lot of time, manpower, and money, and it is difficult to be used universally. Therefore, a virus collection matrix, a manufacturing method of the virus collection matrix, and a detection method for detecting a target virus provided by each embodiment of the present disclosure are applicable to the collection of virus in the environment, and can be used for a follow-up qualitative analysis so as to detect and determine whether the environment has a potential possibility of virus infection. Thus, it can help to establish management and operation systems of conducting early warning and risk management for the target virus such as novel coronavirus.

BRIEF DESCRIPTION OF THE DRAWINGS

FIG. 1 is a schematic diagram of a virus collection matrix according to an embodiment of the present disclosure.

FIG. 2 is an enlarged schematic diagram of real images of a porous gel or fibrous structure according to an embodiment of the present disclosure.

FIG. 3 is a schematic diagram of collecting virus by the virus collection matrix according to an embodiment of the present disclosure.

FIG. 4 is a flowchart of a manufacturing method of virus collection matrix according to an embodiment of the present disclosure.

FIG. 5 is a flowchart of the manufacturing method of the virus collection matrix according to another embodiment of the present disclosure.

FIG. 6 is ultraviolet spectrogram of spectral characteristic peak of the ACE 2 receptors according to an embodiment of the present disclosure.

FIG. 7 is ultraviolet spectrogram of spectral characteristic peak of the spike proteins according to an embodiment of the present disclosure.

FIG. 8 is a flowchart of a detection method using the virus collection matrix to detect the target virus according to an embodiment of the present disclosure.

FIG. 9 is a schematic diagram of an application type of a detection method using the virus collection matrix to detect the target virus according to an embodiment of the present disclosure.

FIG. 10 is a schematic diagram of an application type of using the virus collection matrix to filter airs according to other embodiments of the present disclosure.

DETAILED DESCRIPTION

Various embodiments will be described in detail below, a person skilled in the art may easily understand the spirits and principles of the present disclosure with reference to the drawings and the specification of the present specification. However, although some specific embodiments are described in detail, these embodiments are only described as examples, and shall not be regarded as limitative or exhaustive meanings in any aspects. Therefore, for a person of ordinary skill in the art, various variations and amendments of the present invention may be obvious and may be achieved easily without departing from the spirit and the principle of the present invention.

In order to conduct early warning and risk management of the target virus, an embodiment according to the present disclosure provides a novel virus collection matrix for collecting and filtering virus in the environment and which can be used for follow-up detection analysis. As described above, please refer to FIG. 1, a virus collection matrix 10 according to an embodiment may be formed to be any shapes such as a layer-type; however, the present disclosure is not limited thereto. The virus collection matrix 10 may include a porous gel or fibrous structure 100 and a plurality of ACE 2 receptors (angiotensin converting enzyme 2 receptor) 200 distributed and covered on a surface of the porous gel or fibrous structure 100. In detail, a body of the virus collection matrix 10 may be the porous gel or fibrous structure 100. Please further refer to a real image shown in FIG. 2, the porous gel or fibrous structure 100 may be a solid gel or fibrous network or a solid gel or fibrous structure having porous gap formed by a positively charged polymer material.

Specifically, the porous gel or fibrous structure 100 may be formed by electrostatic force or cross-linking reaction between molecules of the polymer material or electrospinning. The positively charged polymer material, for example, may be chitosan-based polysaccharides, cationic polyacrylates, polyethyleneimine (PEI) and the like; however, the present invention is not limited thereto. For example, the porous gel or fibrous structure 100 may be formed by electrostatic force or EDC cross-linking reaction between molecules of chitosan. In this regard, the orientations of electrostatic force or cross-linking reaction between molecules may be different for each molecule of the polymer material; therefore, disorder aggregation polymer network structures may be produced. Specifically, the porous gel or fibrous structure 100 of the aggregation polymer network structures are filled with a plurality of connection structures having different shapes; therefore, they are filled with porous gaps.

According to the present embodiment, the plurality of ACE 2 receptors 200 may be connected to the porous gel or fibrous structure 100 by electric charge attraction or chemical grafting. Specifically, the porous gel or fibrous structure 100 is formed by the positively charged polymer material; therefore, it is positively charged as a whole. Accordingly, the porous gel or fibrous structure 100 may be connected to the negatively charged ACE 2 receptors 200 by electric charge attraction, so that the plurality of ACE 2 receptors 200 are attached on the surface of the porous gel or fibrous structure 100. In addition, the ACE 2 receptors 200 may also be attached on the surface of the porous gel or fibrous structure 100 by chemical grafting through direct covalent bonds or indirect covalent bonds with other intermediates therebetween. For example, the ACE 2 receptors 200 are chemically coated on the surface the porous gel or fibrous structure 100 by coupling agent.

Figure 2:
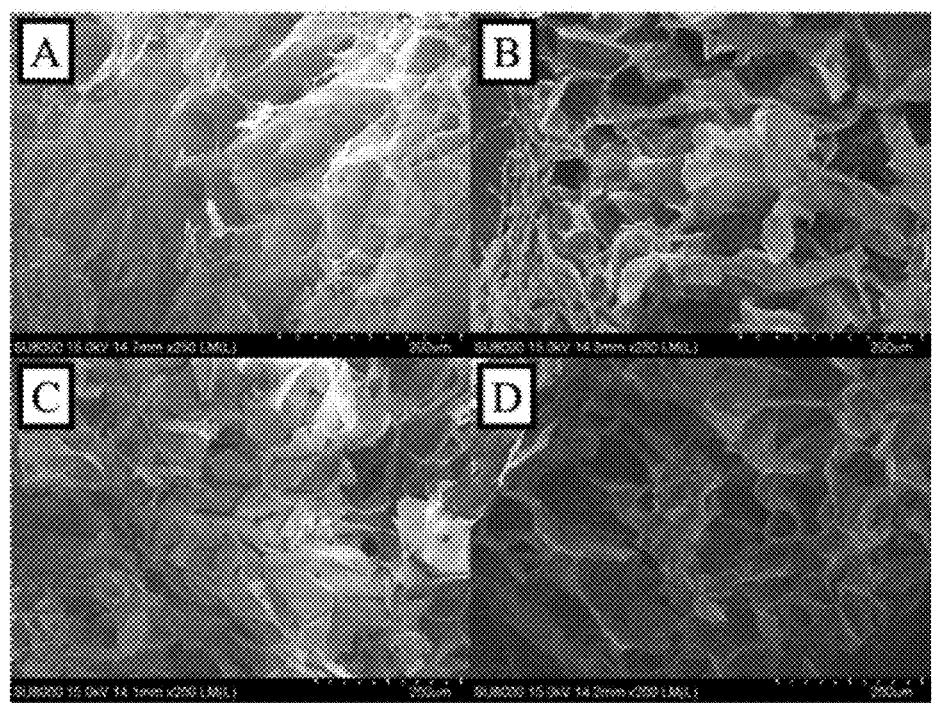

Notably, when it comes to the statement "the plurality of ACE 2 receptors 200 may be attached on the surface of the porous gel or fibrous structure 100", it means that the plurality of ACE 2 receptors 200 may be attached on the surface of any portion of the connection structures of the porous gel or fibrous structure 100 with random shapes rather than that the plurality of ACE 2 receptors 200 are only attached on a side surface of the whole porous gel or fibrous structure 100 toward a single direction. That is, a shape outline drawing of the whole porous gel or fibrous structure 100 illustrated in FIG. 1 is not a real detailed configuration of the porous gel or fibrous structure 100. As shown in FIG. 2, the porous gel or fibrous structure 100 is substantially an aggregation polymer network structures filled with porous gaps and random indefinite changes in structural detail; and the plurality of ACE 2 receptors 200 may be attached on the surface of any portions of the aggregation polymer network structures including a surface of the porous gel or fibrous structure 100 inside porous gaps toward various angles. Hence, according to the present embodiment, a surface area of the porous gel or fibrous structure 100 capable of being attached to the plurality of ACE 2 receptors 200 is substantially increased due to the properties of the porous gaps.

According to some embodiments of the present disclosure, although the plurality of ACE 2 receptors 200 is negatively charged, the whole of the virus collection matrix 10 with the plurality of ACE 2 receptors 200 attached on the porous gel or fibrous structure 100 may be still positively charged since the porous gel or fibrous structure 100 is positively charged. For example, attached amounts of the plurality of ACE 2 receptors 200 may be controlled so that the whole of the virus collection matrix 10 is still positively charged. According to other embodiments, for example, even if the whole surface area is covered with the ACE 2 receptors 200, the whole of the virus collection matrix 10 is still positively charged due to strong positively charged porous gel or fibrous structure 100 formed by chitosan.

Figure 3:
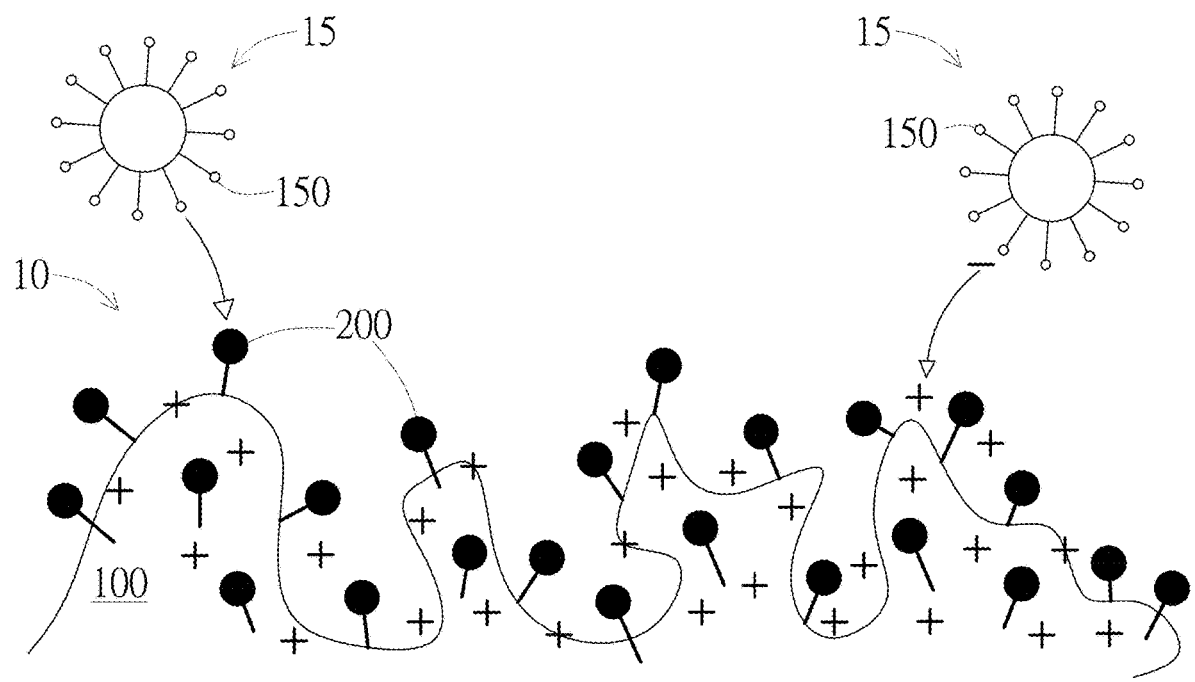

As mentioned above, according to the present embodiment, the virus collection matrix 10 has the plurality of ACE 2 receptors 200. Thus, please further refer to FIG. 3, the virus collection matrix 10 is applicable for collecting target viruses 15 including novel coronavirus (covid-19), SARS virus, or any other coronavirus containing spike protein 150. In detail, when the target virus 15 passes through the virus collection matrix 10, the target virus 15 is capable of being detained on the surface of the porous gel or fibrous structure 100. For example, as shown in FIG. 3, the target virus 15 may be specifically attached to the ACE 2 receptors 200 indirectly through the spike protein 150 so as to be detained on the surface of the porous gel or fibrous structure 100 (through the interaction of the donor-receptor of the ACE 2 receptor 200); or the target virus 15 is capable of being attracted and detained on the surface of the positively charged porous gel or fibrous structure 100 due to the negatively charged property of the target virus 15; or the target virus 15 may be attracted to be approaching the surface of the positively charged porous gel or fibrous structure 100 due to the negatively charged property of the target virus 15 and further attached to the plurality of ACE 2 receptors 200 due to the interaction of the donor-receptor.

Due to the high permeability properties of the porous gaps of the porous gel or fibrous structure 100, contact surface areas between the virus collection matrix 10 having the porous gel or fibrous structure 100 as the main body according to the present embodiment and the target virus 15 or samples which might include the target virus 15 may be substantially increased. Therefore, capability of the virus collection matrix 10 to collect the target virus 15 for detection or other treating processes may be substantially increased. In addition, the virus collection matrix 10 may further have air permeability due to the high permeability properties of the porous gaps. Therefore, the virus collection matrix 10 may be available to capture the target virus 15 in airs through air flow so as to improve effectiveness of capturing and collecting the target virus 15. Thus, the virus collection matrix 10 may be used for capturing and collecting the target virus 15 widespread in air and difficult to be captured so as to increase sensitivity of qualitative analysis for the target virus 15; and continued distribution of the target virus 15 in air is decreased or prevented by intercepting the target virus 15.

Figure 4:
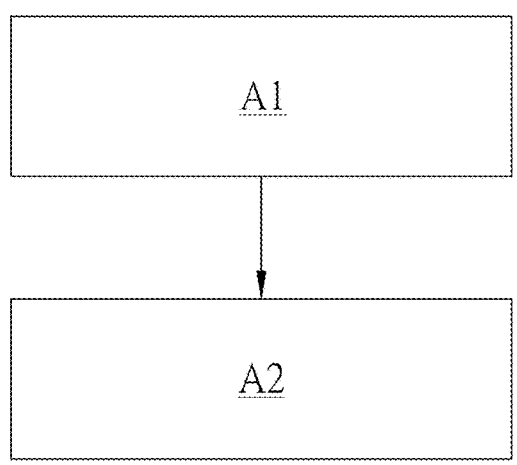

Next, please refer to FIG. 4, a manufacturing method 20 of the virus collection matrix 10 according to an embodiment is further described below as an example.

As indicated above, according to an embodiment of the present disclosure, the manufacturing method 20 of the virus collection matrix 10 may include: a step A1 of forming the porous gel or fibrous structure using the positively charged polymer material, and a step A2 of distributing the ACE 2 receptors to be attached on the formed porous gel or fibrous structure. For example, please refer to FIG. 5, an exemplary manufacturing method 30 according to an embodiment may include: a step A11 of dissolving chitosan into an aqueous solution and adding a little acetic acid to dissolve chitosan completely so as to form a first solution; a step A12 of adding glycerol and beta-glycophosphate into the first solution so as to form a second solution; a step A13 of letting the second solution stand for a predetermined time until cross-linking reaction is proceed in the second solution so as to form the solid gel; a step A14 of lyophilizing the solid gel so as to form the porous gel or fibrous structure as the body of the virus collection matrix; and a step A21 of distributing and covering the plurality of ACE 2 receptors on the surface of the porous gel or fibrous structure and connecting the plurality of ACE 2 receptors to the porous gel or fibrous structure by electric charge attraction or chemical grafting. Alternatively, according to other embodiments, the step A13 and the step A14 can be substituted by a step that the second solution is subjecting under electrostatic fiber-drawing condition, e.g., electrospinning, to form the porous gel or fibrous structure. For example, the second solution can be evolved into ultrafine fibrous mats using an electrospinning equipment, either free standing mats or deposited onto a given substrate.

Figure 5:
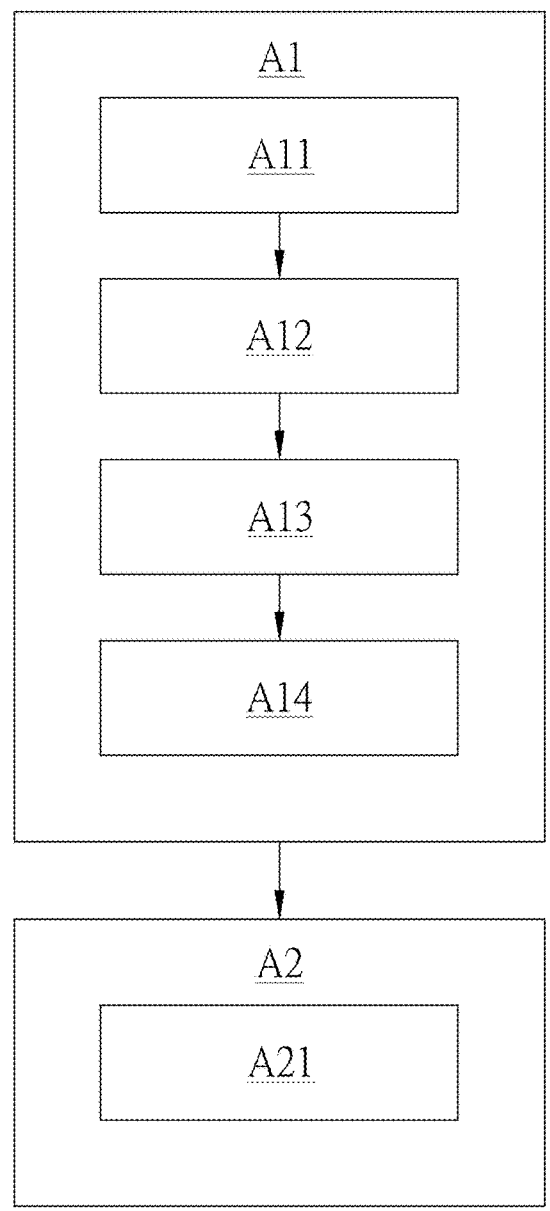

As illustrated above, the porous gel or fibrous structure of the virus collection matrix formed according to an embodiment illustrated in FIG. 5 may have patterns of various actual detailed shapes and features as shown in FIG. 2.

Moreover, the detailed processes illustrated in the manufacturing method 30 merely represents an example, and the present disclosure is not limited thereto. For example, the porous gel or fibrous structure may also be formed of the polymer material through various ways including lyophilization, 3D printing, electrospinning nanofiber, cross-linking reaction, electrochemistry or spray coating. In addition, in order to further stabilize a whole of the porous gel or fibrous structure, it is also possible to manufacture or form the porous gel or fibrous structure in a mold with a specific shape. Alternatively, the virus collection matrix may also further include a carrier, such that the porous gel or fibrous structure may be formed on the carrier and be supported by the carrier. For example, according to some embodiments, the carrier may be a textile fiber or Teflon, and the porous gel or fibrous structure may form a one-layer of porous permeable structure on the carrier. However, all of them are only disclosed as examples, and the present disclosure is not limited thereto.

Furthermore, according to an embodiment of the present disclosure, the virus collection matrix formed by the manufacturing method 30 of the embodiment as shown FIG. 5 may be soaked into the solution containing spike proteins to test the ability of collecting the spike protein and the corresponding target virus.

Figure 6:
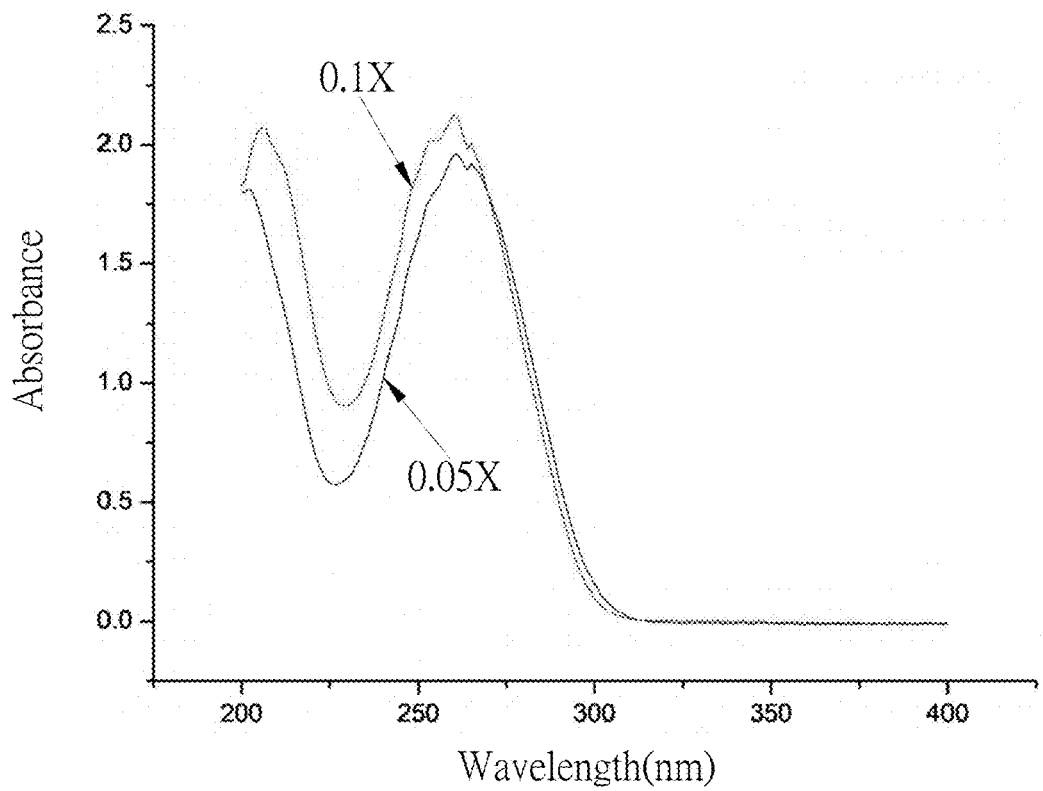
Figure 7:
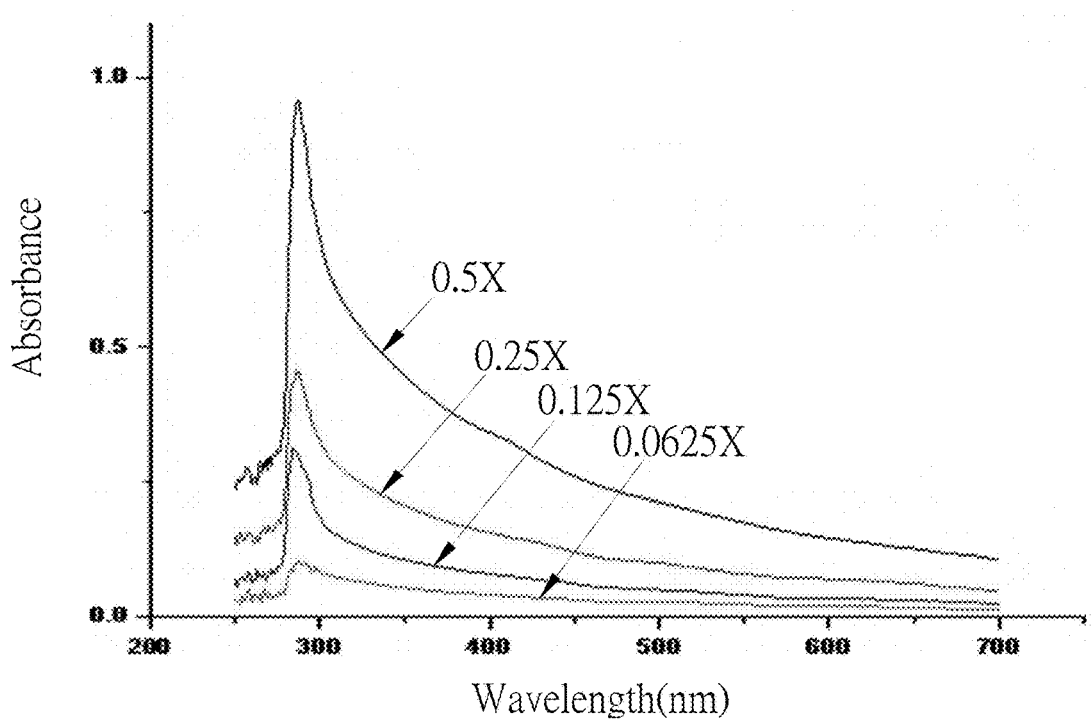

First, please refer to FIG. 6 which illustrates an ultraviolet (UV) spectrum of only the ACE 2 receptors. In detail, FIG. 6 is an UV spectrum showing spectral characteristic peaks of the ACE 2 receptors, wherein a mother liquor of the ACE 2 receptor (4.78 mg/ml) is respectively diluted to 0.1 times and 0.05 times and optical analysis is conducted under a spectrometer. Therefore, dilution of 0.1 times approximately corresponds to the ACE 2 receptor of 50 uM, and dilution of 0.05 times approximately corresponds to the ACE 2 receptor of 25 uM. The spectral characteristic peaks of the ACE 2 receptors are appeared apparently in FIG. 6 for both of them: the absorption peaks of ultraviolet (UV) spectrum at 270 nm. Next, please further refer to FIG. 7 which illustrates an ultraviolet (UV) spectrum of only the spike protein. In detail, FIG. 7 is an ultraviolet (UV) spectrum showing spectral characteristic peaks of spike protein, wherein a mother liquor of the spike protein (1.75 mg/mL) is respectively diluted to 0.5 times, 0.25 times, 0.125 times, and 0.0625 times, and optical analysis is conducted under a spectrometer. Therefore, dilution of 0.5 times approximately corresponds to the spike protein of 0.88 mg/mL, dilution of 0.25 times approximately corresponds to the spike protein of 0.44 mg/mL, dilution of 0.125 times approximately corresponds to the spike protein of 0.22 mg/mL, and dilution of 0.0625 times approximately corresponds to the spike protein of 0.11 mg/mL. The spectral characteristic peaks of the spike protein are appeared apparently in FIG. 7 for all the mentioned concentrations: the absorption peaks of ultraviolet (UV) spectrum at 280-290 nm. In addition, although features of the ultraviolet (UV) spectrums of the spike protein are described as an example since the features of the ultraviolet (UV) spectrums of the spike protein are significant, the present disclosure may otherwise use other spectral characteristic peaks of the spike protein. For example, the feature that absorption peaks of the near infrared spectrum of the spike protein is at 900-1400 nm may otherwise be used as an evidence of optical analysis and qualitative determination. Therefore, spectrometers configured to analyze analyte collected by the virus collection matrix of each embodiment of the present disclosure may be an UV spectrometer, a NIR spectrometer, or any other spectrometers.

According to the present embodiment, the virus collection matrix may be soaked into the solution of the spike protein, then the virus collection matrix (a porous surface) adsorbing the spike protein is directly applied to optical analysis by the UV-Vis spectrometer. For example, in an embodiment, the applicant soaks the virus collection matrix formed by the embodiment as illustrated in FIG. 5 into the solution containing the spike protein of concentration of 1.75 mg/mL and then withdraw the virus collection matrix. The obtained virus collection matrix is experimentally confirmed that the optical analysis by the UV-Vis spectrometer can indeed clearly present the spectral characteristic peaks of the spike protein illustrated in FIG. 7 in addition to the spectral characteristic peaks of the ACE 2 receptors illustrated in FIG. 6. That is, in the actual application, when the target virus containing the spike protein is disposed on the virus collection matrix, the direct optical analysis of the virus collection matrix by the spectrometer will further present the spectral characteristic peaks of the spike protein (please refer to FIG. 7) in addition to the spectral characteristic peaks of the ACE 2 receptors. Accordingly, the optical analysis may be conducted by the obtained virus collection matrix used for collection and the optical analysis result is compared to the spectral characteristic peaks illustrated in FIG. 6 and FIG. 7; when the spectral characteristic peaks matched with FIG. 7 is appeared, it can be qualitatively determined that the virus collection matrix has collected the target virus containing the spike protein.

As mentioned above, after the virus collection matrix formed by the manufacturing method 30 of the embodiment as illustrated in FIG. 5 is soaked into the solution containing the spike protein, the spike protein can be absorbed or fixed effectively, so that the spectral characteristic peaks of the spike protein may be detected by the spectrometer. Therefore, the manufacturing method of the virus collection matrix according to the present embodiment and the manufactured virus collection matrix may be substantially configured to collect the target virus containing the spike protein, and may be further configured to filter the target virus out. In addition, the virus collection matrix which has collected the target virus may also be used for various follow-up detection and analysis. For example, the optical analysis may be conducted by directly disposing the virus collection matrix under UV-Vis or Raman spectrometer to test whether the specific spectral characteristic peaks of the target virus is detected or not; or the analyte may be taken off from the virus collection matrix and/or purified from the virus collection matrix, then the analyte is disposed under the spectrometer and optically analyzed to test whether the specific spectral characteristic peaks of the target virus is detected or not, so as to conduct the Qualitative Analysis to determine whether the virus exists or not. Furthermore, according to the other embodiment of the present disclosure, the virus collection matrix which has collected the target virus is also applicable to other analytic instruments or other analysis methods, such as analysis of protein sequence. Thus, the optical analysis mentioned here is just used as an example, and the present disclosure is not limited thereto.

After the virus collection matrix is in contact with a target of the spike protein, the resolution which can distinguish the spectral characteristic peaks of the spike protein when conducting the optical analysis will be changed along with the used instruments. According to some embodiment of the present disclosure, when the virus collection matrix of each of the mentioned embodiments is used for optical analysis, the detection results shows that the concentration of the resolution with respect to the spike protein may be basically lower than 3.5 uM. For example, when the optical analysis is conducted by the virus collection matrix, the concentration of the resolution with respect to the spike protein may range from 1 uM to 3.5 uM. Furthermore, when the detection analysis is conducted using an advanced spectrometer (for example, but not limited to high resolution UV-Vis spectrometer), according to some embodiments of the present disclosure, when the virus collection matrix of each of the mentioned embodiments is used for optical analysis, the detection results shows that the concentration of the resolution with respect to the spike protein may be further lower to 10 nM to 100 nM, or may be even lower than 10 nM.

As mentioned above, the virus collection matrix according to each embodiments of the present disclosure may be configured to collect virus, and may configured to filter the virus out, or further used for the various follow-up detection and analysis. Therefore, the virus collection matrix may be configured to be combined to other devices or equipments so as to filter air, collect virus, or conduct the combination thereof when air flows through. For example, the virus collection matrix may be a chip or a filter material. For example, the virus collection matrix may be a chip and disposed on a device or an equipment through which air passes, so that the target virus in air is collected when the air pass through the device or the equipment. According to some embodiments, the virus collection matrix according to each embodiment of the present disclosure may use the air flow passing in and out caused by breathing, actions, or powers of the device or the equipment itself to collect the virus with respect to the device or the equipment, and may be taken off from the device or the equipment to conduct follow-up detection and analysis. Alternatively, the virus collection matrix may be a filter material and disposed on a device or an equipment through which air passes, so that the target virus in air is collected when the air pass through the device or the equipment. For example, the virus collection matrix according to each embodiment of the present disclosure may use the air flow passing in and out caused by breathing, actions, or powers of the device or the equipment itself to filter the virus out with respect to the device or the equipment. However, the virus collection matrix may also be applied without connecting to any device or equipment, and may be used individually for conducting air filtering, virus collection, or combination thereof.

Hereinafter, a detection method for detecting the target virus using the virus collection matrix according to an embodiment of the present disclosure will be further described referring to FIG. 8 and FIG. 9.

Figure 8:
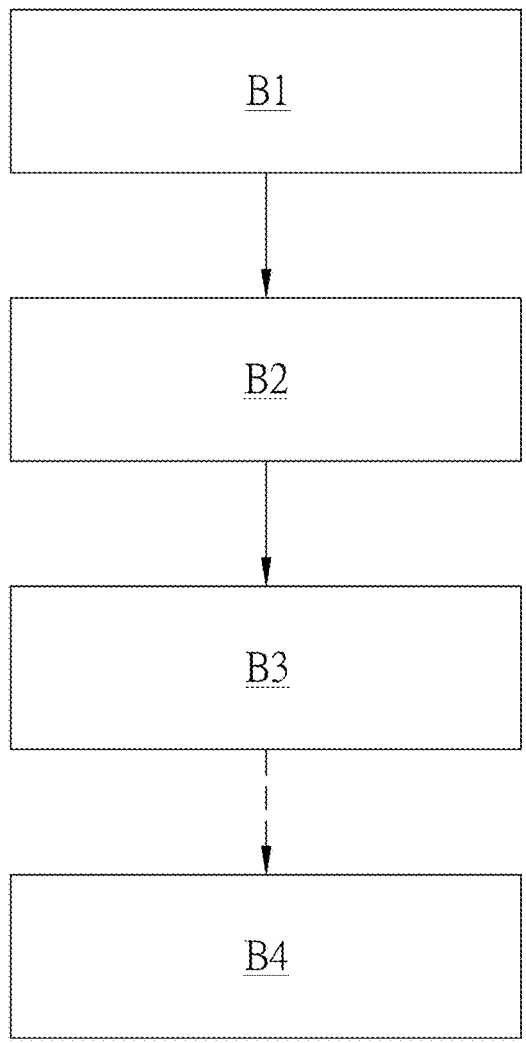

FIG. 8 is a flowchart exemplarily illustrating a detection method 40 for detecting the target virus according to an embodiment. Specifically, the detection method 40 for detecting the target virus may include: a step B1 of disposing the virus collection matrix according to any one of the mentioned embodiments under a test environment within a predetermined duration; a step B2 of withdrawing the virus collection matrix, and conducting optical analysis to the virus collection matrix directly or conducting optical analysis to an analyte absorbed on the virus collection matrix after taking off the analyte; and a step B3 of determining whether the spectral characteristic peaks of the spike protein is detected or not so as to determine whether the target virus containing the spike protein exists in the test environment or not.

Figure 9:
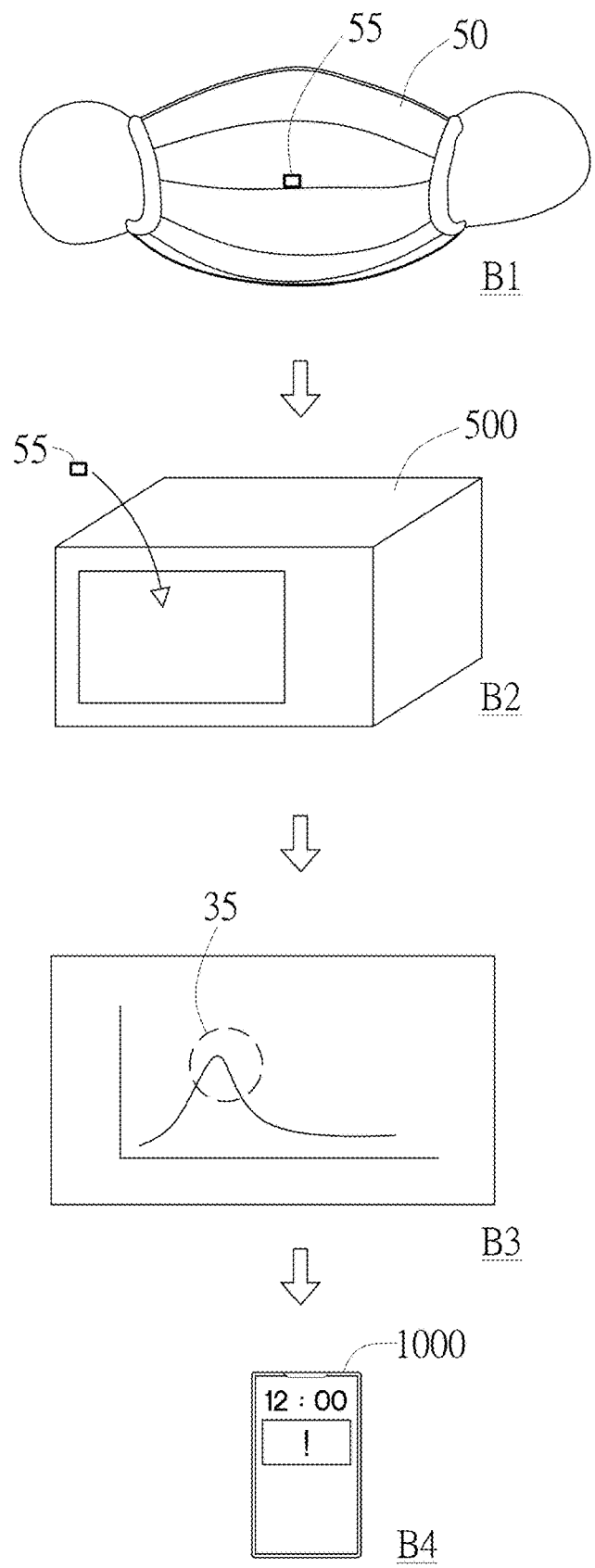

For example, please further refer to FIG. 9 exemplarily illustrating implementation and application respectively corresponding to each steps of FIG. 8. Specifically, as shown in FIG. 9, the virus collection matrix may be fixed into a face mask 50 in a form of a chip 55 in the step B1. The face mask 50 may be worn by a specific person in a specific place within a predetermined duration such as a whole day. Then, in the step B2, the chip 55 on the face mask 50 may be withdrawn and optical analysis is conducted to the chip 55 directly by a spectrometer 500; and in the step B3, it is determined whether the chip 55 present the spectral characteristic peaks 35 of the spike protein or not in accordance with a spectrum result analyzed based on the spectrometer so as to determine whether the target virus containing the spike protein such as novel coronavirus existed or not in the specific place at that day.

In addition, please refer to FIG. 9 together with FIG. 8, the detection method according to an embodiment of the present disclosure may also further include a step B4 of transmitting a result to a device of a target person after determining whether the spectral characteristic peaks of the spike protein is detected or not, so as to conduct notification, or early warning to the target person that the target virus exists in the test environment during the predetermined duration. Specifically, as shown in FIG. 9, after determining that the spectral characteristic peaks 35 of the spike protein is detected, the results may be transmitted to a smartphone 1000 of the specific person wearing the face mask 50 on that day, so as to conduct notification or early warning to the specific person that the specific person might be in contact with a patient or an object infected with the novel coronavirus in the specific place at that day. Thus, it is possible to trace, and to find out patients infected with the virus earlier or to make the specific person being aware of risk of being in contact with the target virus earlier by collaboration of optical analysis and information transmission. Therefore, it is possible to conduct early warning of the individual risk of infection or management of the individual health status more sensitively with lower cost, and it can be helpful for establishing a point-of-care system or a personalized care system.

According to some embodiment of the present disclosure, for example, when the chip 55 is disposed on a device or an equipment in the public place, after the chip 55 is taken off and a result that the target virus might exist is detected, the informed target people may be people who were in the test environment during the predetermined duration traced by a navigation system. For example, in the case of the target virus being detected through the virus collection matrix in the specific test environment during the predetermined duration and therefore a risk of infection occurs, the government may release warning messages to all of the people having records to have visited the specific test environment during the predetermined duration, so as to raise alertness of people for epidemic prevention. However, the informed target people illustratively mentioned in the specification merely represents examples, and the present disclosure is not limited thereto; in addition, the informed or warned people are adjustable in accordance with various application situation freely and flexibly.

Figure 10:
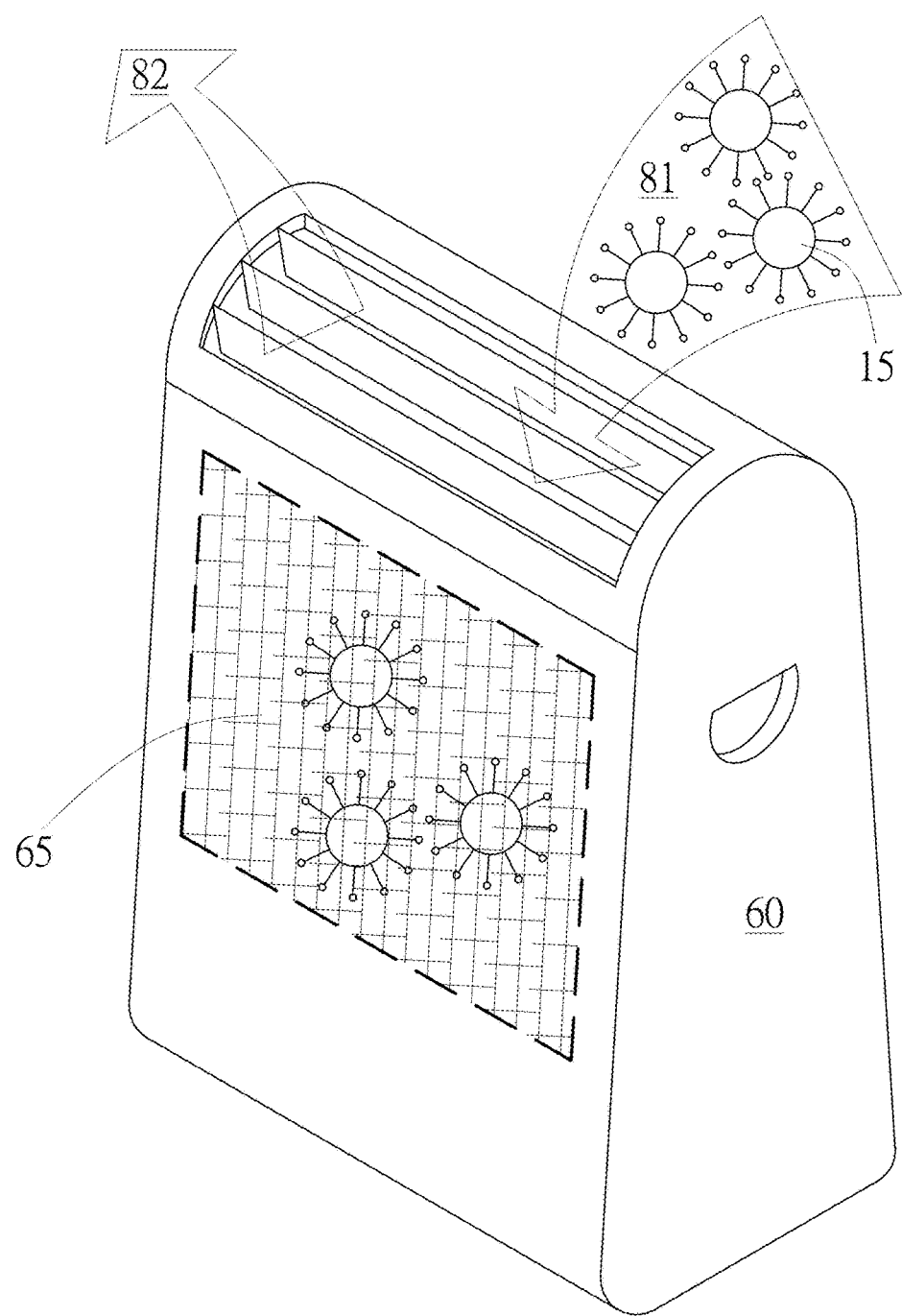

Furthermore, according to other embodiments of the present disclosure, please refer to FIG. 10, for example, the virus collection matrix in each of the mentioned embodiments may be directly used as a filter material 65 of an air purifier 60. Therefore, when polluted air 81 containing the target virus 15 which might have risks of causing human infection and illness exists in the environment, the target virus 15 may be detained on the filter material 65 through the filter material 65 of the air purifier 60. Therefore, the target virus 15 can be decreased or removed completely in filtered air 82 passing and exhausted through the filter material 65, so as to decrease risks and possibilities of people getting infected by the virus in the environment.

Moreover, according to some embodiments, when it is essential to increase sensitiveness of detection by collecting the virus, a smaller size of virus collection matrix may be used so as to be beneficial for concentrating the concentration of the captured target virus; and when it is essential to filter the virus out so as to avoid unexpected spread of the target virus, a larger size of virus collection matrix may be used. However, thoses cases merely represent examples, and all of sizes, shapes, and patterns of the virus collection matrix are variable and adjustable in accordance with the using application situation; and the present disclosure is not limited to examples described in detail herein.

As mentioned above, the virus collection matrix, the manufacturing method of the virus collection matrix, and a detection method for detecting the target virus according to each embodiment of the present disclosure may filter the virus out and/or collect and concentrate the virus, and may be used for follow-up detection analysis. Therefore, it may be helpful for establishing systems configured to conduct determination, management, and early warning of risks of virus infection before the individual infection occurs.

The mentioned contents merely represent some preferred embodiments of the present disclosure. Please note that various changes and modifications of the present disclosure are allowed without departing from the conception and principles of the present invention. A person of skilled in the art should understand that the scope of the present disclosure is defined by the appended claims, and various replacements, combinations, modifications, and conversions based on intention of the present disclosure all fall within the scope defined by the appended claims of the present invention.

REFERENCE NUMERALS

10: virus collection matrix
15: target virus
20, 30: manufacturing method
35: spectral characteristic peak
40: detection method
50: face mask
55: chip
60: air purifier
65: filter material
81: polluted air
82: filtered air
100: porous gel or fibrous structure
150: spike protein
200: ACE 2 receptor
500: spectrometer
1000: smartphone
A1, A11, A12, A13, A14, A2, A21, 131, 132, 133, 134: step

What is claimed is:

1. A virus collection matrix for collecting target virus in air, comprising:
 a porous gel or fibrous structure formed by a positively charged polymer material; and
 a plurality of ACE 2 receptors, the plurality of ACE 2 receptors are negatively charged, and distributed and covered on a surface of the porous gel or fibrous structure, and
 wherein a whole of the virus collection matrix comprising the negatively charged ACE 2 receptors is positively charged.

2. The virus collection matrix according to claim 1, wherein the polymer material is chitosan, and the porous gel or fibrous structure is formed by electrostatic force or EDC cross-linking reaction between molecules of chitosan.

3. The virus collection matrix according to claim 1, wherein the plurality of ACE 2 receptors are connected to the porous gel or fibrous structure by electric charge attraction or chemical grafting.

4. The virus collection matrix according to claim 1, wherein the virus collection matrix is applicable for collecting the target viruses including novel coronavirus (covid-19), SARS virus, or any other coronavirus containing spike proteins, and when the target virus passes through the virus collection matrix, the target virus is capable of being detained on the surface of the porous gel or fibrous structure.

5. The virus collection matrix according to claim 4, wherein in response to the virus collection matrix detaining the target virus, the virus collection matrix exhibits a spectral characteristic peak of the spike proteins when being optically analyzed by a spectrometer.

6. The virus collection matrix according to claim 5, wherein the virus collection matrix exhibits an absorption peak of ultraviolet spectrum at 280-290 nm, and an absorption peak of near infrared spectrum at 900-1400 nm.

7. The virus collection matrix according to claim 5, wherein the virus collection matrix exhibits a concentration of resolution with respect to the spike proteins is lower than 3.5 uM when being optically analyzed.

8. The virus collection matrix according to claim 5, wherein the virus collection matrix exhibits a concentration of resolution with respect to the spike proteins lower than 10 nM when being optically analyzed.

9. The virus collection matrix according to claim 1, wherein the virus collection matrix is a chip or a filter material.

10. The virus collection matrix according to claim 1, wherein the virus collection matrix is configured to be combined to other device or equipment so as to filter air, collect virus, or conduct combination thereof when air flows through.

11. The virus collection matrix according to claim 1, wherein the porous gel or fibrous structure is formed of the polymer material through lyophilization, 3D printing, electrospinning nanofiber, cross-linking reaction, electrochemistry or spray coating.

12. The virus collection matrix according to claim 1, wherein the virus collection matrix further includes a carrier, and the porous gel or fibrous structure is formed on the carrier.

13. The virus collection matrix according to claim 12, wherein the carrier is a textile fiber or teflon.

* * * * *